United States Patent [19]

D'Silva

[11] 4,413,007
[45] Nov. 1, 1983

[54] PESTICIDAL SYMMETRICAL N-SUBSTITUTED BIS-CARBAMOYLOXIMINO DISULFIDE COMPOUNDS

[75] Inventor: Themistocles D. J. D'Silva, South Charleston, W. Va.

[73] Assignee: Union Carbide Corporation, Danbury, Conn.

[21] Appl. No.: 934,973

[22] Filed: Aug. 18, 1978

Related U.S. Application Data

[62] Division of Ser. No. 781,997, Mar. 28, 1977, Pat. No. 4,327,110.

[51] Int. Cl.$^3$ .................... A01N 33/02; C07C 121/50; C07C 125/06; C07C 119/20
[52] U.S. Cl. ................ 424/298; 260/465 D; 424/304; 260/465.4; 260/453.3; 564/100
[58] Field of Search ......... 260/465 D, 566 AC, 465.4, 260/453.3; 424/304, 298; 564/100

[56] References Cited

U.S. PATENT DOCUMENTS

| | | | |
|---|---|---|---|
| 3,819,649 | 6/1974 | Zumach | 260/327 M |
| 3,890,386 | 6/1975 | Kuhle et al. | 260/566 AC |
| 3,947,591 | 3/1976 | Rizzo et al. | 260/551 S X |
| 3,992,549 | 11/1976 | Durden et al. | 424/277 |
| 3,998,963 | 12/1976 | Durden et al. | 424/298 |
| 4,004,031 | 1/1977 | Drabek | 260/566 AC X |

OTHER PUBLICATIONS

Fahmy, et al., 22 (1974), J. Agr. Food Chem., pp. 59–62.

*Primary Examiner*—Henry R. Jiles
*Assistant Examiner*—Robert C. Whittenbaugh
*Attorney, Agent, or Firm*—Robert C. Brown; Clement J. Vicari; William R. Moran

[57] ABSTRACT

Symmetrical N-substituted bis-carbamoyloximino disulfide compounds exhibit outstanding nematocidal, miticidal and insecticidal activity, coupled with substantially reduced mammalian toxicity and phytotoxicity as compared to known pesticidal compounds having a comparable spectrum of activity against insect, arachnid and nematode pests.

29 Claims, No Drawings

PESTICIDAL SYMMETRICAL N-SUBSTITUTED BIS-CARBAMOYLOXIMINO DISULFIDE COMPOUNDS

This application is a division of our prior U.S. application Ser. No. 781,997 filing date Mar. 28, 1977 now U.S. Pat. No. 4,327,110.

This invention relates to symmetrical N-substituted bis-carbamoyloximino disulfide compounds and to methods for preparing the same. This invention is also directed to insecticidal, miticidal and nematocidal compositions comprising an acceptable carrier and an insecticidally, miticidally or nematocidally effective amount of a compound according to this invention, as well as to a method of controlling insects, mites and nematodes by subjecting them to an insecticidally, miticidally or nematocidally effective amount of a compound of this invention.

More particularly, this invention relates to compounds of the formula:

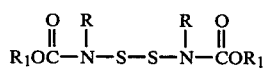

wherein:

R is alkyl having from 1 to 4 carbon atoms;
$R_1$ is:

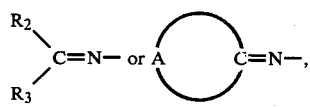

wherein:

$R_2$ is hydrogen, chloro, cyano, alkyl, alkylthio or cyanoalkylthio;

$R_3$ is alkyl, alkylthio, alkoxy, alkanoyl, benzoyl, alkoxycarbonyl, alkylsulfonyl, alkylsulfinyl, alkenyl, alkynyl or phenyl all of which may be substituted with one or more cyano, nitro, fluoro, bromo, chloro, alkylthio, alkylsulfinyl, alkylsulfonyl, alkoxy, phenoxy, carbamoyl, alkylcarbamoyl, dialkylcarbamoyl or

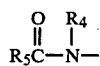

wherein:

$R_4$ is hydrogen or alkyl;
$R_5$ is hydrogen, alkyl, alkoxy or alkylthio;

A is a divalent alkylene chain having from 2 to 24 aliphatic carbon atoms completing a five or six membered alicyclic ring which includes one, two or three groups selected from the group consisting of divalent oxygen, sulfur, sulfinyl, sulfonyl, amino, alkylamino or carbonyl groups in any combination;

with the proviso that $R_2$, $R_3$, $R_4$ and $R_5$ substituents inidividually may not include more than eight aliphatic carbon atoms.

The following miticidally, insecticidally and nematocidally active compounds are illustrative of the compounds of this invention all of which can be conveniently prepared by the process of this invention simply by selecting appropriate starting materials for use in the procedures described below:

N,N'-bis-[1-Methylthioacetaldehyde O-(N-methylcarbamoyl)oxime]disulfide
N,N'-bis-[1-Isopropylthioacetaldehyde O-(N-methylcarbamoyl)oxime]disulfide
N,N'-bis-[1-(2-Cyanoethylthio)acetaldehyde O-(N-methylcarbamoyl)oxime]disulfide
N,N'-bis-[5-Methyl-4-(O-(N-methylcarbamoyl)oximino)-1,3-oxathiolane]disulfide
N,N'-bis-[2-(O-(N-Methylcarbamoyl)-1,4-dithiane]disulfide
N,N'-bis-[4-(O-(N-Methylcarbamoyl)oximino)-1,3-dithiolane]disulfide
N,N'-bis-[5,5-Dimethyl-4-(O-(N-methylcarbamoyl)oximino)-1,3-dithiolane]disulfide
N,N'-bis-[3,5,5-Trimethyl-2-(O-(N-methylcarbamoyl)oximino)-thiazolidin-4-one]disulfide
N,N'-bis-[4,5,5-Trimethyl-2-(O-(N-methylcarbamoyl)oximino)-thiazolidin-3-one]disulfide
N,N'-bis-[2-(O-(N-Methylcarbamoyl)oximino)-1,3-dithiolane]disulfide
N,N'-bis-[2-Cyano-2-methylpropionaldehyde O-(N-methylcarbamoyl)oxime]disulfide
N,N'-bis-[1-Methylthio-N'',N''-dimethylcarbamoyl formaldehyde O-(N-methylcarbamoyl)oxime]disulfide
N,N'-bis-[4-Methyl-2-(O-(N-methylcarbamoyl)oximino)tetrahydro-1,4-thiazin-3-one]disulfide
N,N'-bis-[3,3-Dimethyl-1-methylthiobutanone-2 O-(N-methylcarbamoyl)oxime]disulfide
N,N'-bis-[3-Methylsulfonylbutanone-2 O-(N-methylcarbamoyl)oxime]disulfide
N,N'-bis-[2-Methylsulfonyl-2-methylpropionaldehyde O-(N-methylcarbamoyl)oxime]disulfide
N,N'-bis-[1-Methylthiopyruvaldehyde O-(N-methylcarbamoyl)oxime]disulfide
N,N'-bis-[3,3-Dimethyl-1-methylsulfonylbutanone-2-O-(N-methylcarbamoyl)oxime]disulfide
N,N'-bis-1-[N-(Dimethylaminomethylene)carbamoyl]-1-methylthioformaldehyde O-(N-methylcarbamoyl)oxime]disulfide
N,N'-bis-[1-Methylthio-1-ethoxycarbonylformaldehyde O-(N-methylcarbamoyl)oxime]disulfide
N,N'-bis-[1,3,5-Oxadithiane-4 O-(N-methylcarbamoyloximino)]disulfide
N,N'-bis-[(O-(N-Methylcarbamoyl)oximino-1,4-oxathiane]disulfide
N,N'-bis-[1-Cyano-2,2-dimethylpropionaldehyde O-(N-methylcarbamoyl)oxime]disulfide
N,N'-bis-[4-Methyl-2-(O-(N-methylcarbamoyl)oximino)tetrahydro-1,4-thiazin-5-one]disulfide
N,N'-bis-[1-Methylthioacetaldehyde O-(N-butylcarbamoyl)oxime]disulfide
N,N'-bis-[1,3,5-Trithiane-2 O-(N-methylcarbamoyl)oximino]disulfide All of the compounds within the purview of the generic formula set forth above exhibit nematocidal, miticidal and insecticidal activity to a lesser or greater extent. Accordingly, these compounds are extremely useful for the control of insect, nematode and mite pests. Some of these compounds exhibit very high levels of miticidal, nematocidal and insecticidal activity in extremely small dosages while others require larger dosages to be effective.

In general, the compounds of this invention are either totally lacking in phytotoxicity or exhibit only minimal phytotoxicity with respect to economically important crop species. In addition, these compounds exhibit substantially reduced levels of mammalian toxicity as compared to known pesticidal compounds having a comparable spectrum of activity against insect, arachnid and nematode pests.

Preferred because of their higher levels of miticidal, insecticidal and nematocidal activity are the compounds of this invention in which:
R is methyl;
$R_1$ is

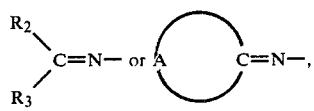

wherein
$R_2$ is hydrogen, alkyl, alkylthio or cyanoalkylthio;
$R_3$ is alkyl, alkylthio, alkylsulfinyl, alkylsulfonyl, alkoxycarbonyl, carbamoyl, alkylcarbamoyl, dialkylcarbamoyl alkylthioalkyl, alkylsulfinylalkyl, alkylsulfonylalkyl, cyanoalkyl, nitroalkyl, cyanoalkyl, nitroalkyl, cyanoalkylthio, cyanoalkylsulfinyl or cyanoalkylsulfonyl.

A is a divalent alkylene chain having from 2 to 24 aliphatic carbon atoms completing a 2-oximino-1, 4-dithiane, 2-oximino-1, 3-dithiane, 4-oximino-1, 3-dithiolane; 2-oximino-1, 4-dioxane; 2-oximino-tetrahydro-1, 4-thiazine-3-one; 2-oximino-1, 3-dithiolane; 2-imino-4-oximino-1, 3-dithiolane; 3-oximinothiophane; 2-oximinothiophane; 2-oximino-tetrahydro-1, 4-oxazin-3-one; 2-oximino-1,3,5-trithiane; 4-oximino-1,3,5-oxathiane; 2-oximino-1, 4-oxathiane; 4-oximino-1, 3-oxathiolane; 2-oximino-thiazoidin-3-one; 2-oximino-1, 3-thiazolidin-4-one or 2-oximino-tetrahydro-1, 4-thiazine-5-one ring systems, wherein sulfur may be in any of its oxidation states. The symmetrical N-substituted bis-carbamoyloximino disulfide compounds of this invention can be prepared by a variety of methods. One preferred method is illustrated by the reaction scheme set forth below in which R and $R_1$ are as described above:

METHOD I

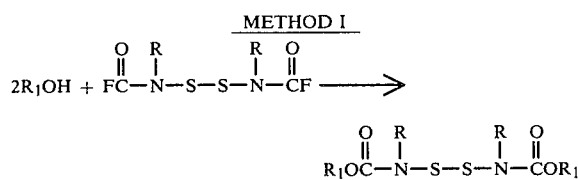

In the procedure illustrated in METHOD I two equivalents of the oxime reactant are reacted with one equivalent of the bis-(fluorocarbonylamino)disulfide reactant in an appropriate solvent in the presence of at least two equivalents of an acid acceptor. Normally, an aprotic organic solvent is employed as the reaction medium. Illustrative of aprotic organic solvents which are suitable as reaction solvents in the practice of the preferred embodiments of this invention are saturated and unsaturated aliphatic and aromatic hydrocarbons, e.g. hexane, cyclohexane, octane, dodecane, naphtha, decalin, kerosene, tetrahydronapthalene, cycloheptane, alkylcycloalkane, benzene, toluene, xylene, naphthalene, alkylnapthalene, or the like; ethers such as tetrahydrofuran, tetrahydropyran, diethyl ether, dioxane, 1, 2-dimethoxybenzene, 1, 2-ethoxybenzene, the mono and dialkyl ethers of ethylene glycol, of dipropylene glycol, of butylene glycol, of diethylene glycol, of dipropylene glycol, or chlorinated aliphatic hydrocarbons as for example, chloroform, dichloromethane, methylene dichloride, 1, 1-dichloroethane, carbon tetrachloride or the like.

The acid acceptor utilized in the conduct of the reaction of METHOD I may be either an organic or inorganic base. Illustrative of organic bases that are useful as acid acceptors are tertiary amines, alkali metal alkoxides or the like. Bases such as sodium hydroxide, potassium hydroxide or the like are illustrative of inorganic bases which are useful in the conduct of this reaction. Preferred acid acceptors are aromatic and aliphatic tertiary amines, such as triethylamine, pyridine, trimethylamine, 1, 4-diazobicyclo[2.2.2]octane and the like.

When an inorganic base is used as the acid acceptor, phase transfer agents may be used to facilitate the transfer of the acid acceptor across the organic/inorganic phase interface. Illustrative of useful phase transfer agents are crown ether compounds, quaternary ammonium halide compounds or the like.

The reaction temperature is not critical and can be varied over a wide range. The reaction is preferably conducted at a temperature of from about $-30°$ C. and upwards to approximately 120° C. Particularly preferred reaction temperatures are from about 0° C. to about 75° C.

Reaction pressures are not critical. The process can be conducted at either subatmospheric, atmospheric or superatmospheric pressure. For convenience the reaction is usually conducted at atmospheric or autogeneous pressure.

Compounds of this invention in which $R_2$, $R_3$ or A includes a sulfinyl or sulfonyl moiety can be conveniently prepared by the selective oxidation of the sulfide linkage of the corresponding thio compound at an appropriate point in the synthetic procedure. For example, N,N'-bis-[2-methylsulfonyl-2-methylpropionaldehyde O-(N-methylcarbamoyl)oxime]disulfide can be conveniently prepared either by selectively oxidising 2-methylthio-2-methylproiona]doxime with peracetic acid prior to carbamoylation or by selectively oxidising N,N'-bis-[2-methylthio-2-methylpropionaldehyde O-(N-methylcarbamoyl)oxime]disulfide subsequent to carbamoylation.

Oxime precursors of the formula:

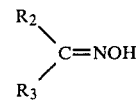

in which $R_2$ and $R_3$ are described above, can be conveniently prepared according to a variety of methods. For example, 2-methylthio-2-methylpropionaldoxime can be prepared by chlorinating 2-methylpropanal to form 2-chloro-2-methylpropanal which is then treated with sodium methylmerceptide to form 2-methylthio-2-methyl-propanal. 2-Methylthio-2-methyl-propanal is then treated with hydroxylamine hydrochloride to form the desired oxime precursor. The above disclosed method together with other methods useful for preparing oxime precursors are described in more detail in the U.S. Pat. Nos. 3,843,669; 3,217,036; 3,217,037; 3,400,153; 3,536,760; 3,576,843 and 3,790,560 and Belgium Pat. No. 813,206.

Alicyclic oxime precursors of the formula:

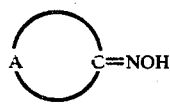

used in the preparation of the disulfide compounds of this invention can be prepared by a variety of methods, the choice of method being influenced to a large extent by the types and number of hetero groups included within the alicyclic ring. For example:

A. 2-oximino-1, 3, 5-trithiane, 4-oximino-1, 3-oxazolidin-4-one, 4-oximino-1, 3,5-oxadithiane and 2-oximino-1,4-oxazine-3-one compounds can be conveniently prepared by sequentially treating the corresponding 1,3,5-trithiane, 1,3-oxazolidin-4-one, 1,3,5-oxadithiane or 1,4-oxazin-3-one compound with a base and an alkyl nitrite ester followed by neutralization with a suitable organic or inorganic acid. For example, 2-oximino-4-methyltetrahydro-1, 4-oxazin-3-one can be prepared by treating 4-methyltetrahydro-1, 4-oxazin-3-one with potassium t-butoxide followed by the addition of isobutyl nitrite. The reaction is conducted in anhydrous tetrahydrofuran. After the reaction has gone to completion in about 3 hours the resulting oxime salt is neutralized with hydrochloric acid.

B. 2-Oximino-tetrahydro-1, 4-thiazine-3-one compounds can be prepared by reacting ethoxycarbonylformhydroxyamoyl chloride with the sodium salt of an appropriately substituted alkylaminoalkane mercaptan in an aprotic solvent, such as benzene, chloroform and the like. This reaction is described in more detail in U.S. Pat. No. 3,790,560.

C. 3-Oximino-1, 4-oxathiane and 4-oximino-1, 3-oxathiolane compounds can be prepared by sequentially treating bis(2-bromoalkyl)ether with sodium nitrile and sodium thioacetate to form 2-(2-acetylthioalkoxy)-1-nitroalkane, which is then treated with sodium hydroxide.

D. 4-Oximino-1, 3-dithiolane and 2-oximino-1, 4-dithiane compounds can be prepared by reacting equivalent amounts of 2-haloalkanehydroxamoyl halide with the sodium salt of an appropriately substituted alkanedithiol in an aprotic solvent like benzene, methylene chloride or ethanol. For example, 2-oximino-3,3-dimethyl-1,4-dithiane can be prepared by adding 1,2-ethanedithiol to sodium ethoxide, thereby producing the sodium salt of 1,2-ethanedithiol in situ and then achieving cyclization by the addition of 2-chloro-2-methylpropionhydroxamoyl chloride.

The bis-(N-alkyl-N-fluorocarbonylamino)disulfide precursors can be conveniently prepared by reacting sulfur monochloride with N-alkylcarbamoyl fluoride in toluene in the presence of an acid acceptor as for example triethylamine or pyridine. This procedure is described in more detail in U.S. Pat. No. 3,639,471.

The following specific examples are presented to particularly illustrate the invention:

EXAMPLE I

Preparation of N,N'-Bis-[1-Methylthioacetaldehyde O-(N-methylcarbamoyl)oxime]disulfide To a solution of 3.25 g of bis-(N-methyl-N-fluorocarbonylamino)disulfide and 3.15 g of 1-methylthioacetaldoxime in 75 ml of toluene was added 3.06 g of triethylamine. After stirring for 20 hrs, the crude reaction mixture was filtered and the filtrate was washed with water, dried over magnesium sulfate and was concentrated to a residual oil. Crystallization from isopropylether-ethylacetate afforded 2.0 g of a white solid m.p. 87°-89° C.
Cal'd for $C_{10}H_{18}N_4O_4S_4$: C, 31.07; H, 4.69; N, 14.50. Found: C, 31.01; H, 4.76; N, 14.24.

EXAMPLE II

Preparation of N,N'-Bis-[1-(2-Cyanoethylthio)acetaldehyde O-(N-methylcarbamoyl)oxime]disulfide To a solution of 3.5 g of 1-(2-cyanoethylthio)acetaldoxime and 2.64 g of bis-(N-methyl-N-fluorocarbonylamino)disulfide in 100 ml of toluene was added 2.46 g of triethylamine. After stirring over-night at room temperature, the reaction mixture was diluted with water and methylene chloride. The organic layer was further washed with water, dried over magnesium sulfate and concentrated to a residual oil. Dry column chromatography afforded 2.0 g of an amorphous solid.
Calc'd for $C_{14}H_{20}N_6O_4S_4$: C, 36.19; H, 4.34; N, 18.09. Found: C, 35.38; H, 4.30; N, 17.56.

EXAMPLE III

Preparation of N,N'-Bis-[2-Methylsulfonyl-2-methylpropionaldehyde O-(N-methylcarbamoyl)oxime]disulfide To a solution of 4.0 g of 2-methylsulfonyl-2-methylpropionaldoxime in 100 ml of toluene was added 2.63 g of bis-(N-Methyl-N-fluorocarbonylamino)disulfide followed by 2.45 g of triethylamine. After stirring for 6 days at room temperature, the solid was filtered and taken in methylene chloride. The solution was washed with water, dried and concentrated to a residual solid. Crystallization from methylene chloride afforded 4.03 g of a solid m.p. 130°-132° C.
Calc'd for $Cl_1H_{26}N_4O_8S_4$: C, 33.19; H, 5.17; N, 11.06. Found: C, 33.25; H, 5.08; N, 10.93.

EXAMPLE IV

Preparation of N,N'-Bis-[1,4-Dithiane-2-O-(N-methylcarbamoyl)oximino]disulfide

To a suspension of 2.98 g of 2-oximino-1,4-dithiane in 200 ml of toluene was added 2.16 g of bis-(N-methyl-N-fluorocarbonylamino)disulfide followed by dropwise addition of 2.02 g of triethylamine. When all the base was added, the oxime was completely in solution. After stirring for 16 hours at room temperature the precipitated solid was filtered and dissolved in methylene chloride. The organic solution was washed with water and dried over magnesium sulfate. Concentration under reduced pressure and crystallization from ethylacetate-methylene chloride afforded 2.9 of a solid. m.p. 142°-143° C.
Calc'd for $C_{12}H_{18}N_4O_4S_6$: C, 30.36; H, 3.82; N, 11.80 Found: C, 30.44; H, 3.72; N, 11.84.

EXAMPLE V

Preparation of N,N'-Bis-[1-Isopropylthioacetaldehyde O-(N-methylcarbamoyl)oxime]disulfide To a solution of 4.07 grams of bis-(N-methyl-N-fluorocarbonylamino)disulfide and 5.0 grams of 1-isopropylthio acetaldoxime in 150 ml of toluene was added 3.79 grams of triethylamine. The reaction mixture was heated with stirring for eight hours at 70° C., followed by stirring over night at room temperature. The reaction mixture was washed with diluted sodium hydroxide followed by water, dried over magnesium sulfate and concentrated to a residual oil. Dry column chromatograph afforded 6.0 grams of a yellow oil.

Calc'd for $C_{14}H_{26}N_4O_4S_4$: C, 37.99; H, 5.92; N, 12.66. Found: C, 37.99; H, 6.01; N, 12.43.

Selected species of the new compounds were evaluated to determine their pesticidal activity against nematodes, mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°–70° F. and 50–70 percent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which tested 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Test

Larvae of the southern armyworm (*Prodenia eridania*, (Cram.)), reared on Tendergreen bean plants at a temperature of 80±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which tested 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. The application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.) reared according to the specifications of the Chemical Specialities Manufacturing Association (Blue Book, McNair-Dorland Co., N.Y. 1954; pages 243–244, 261) under controlled conditions of 80±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80±5° F. and the relative humidity of 50±5 percent. Flies which showed no sign of movement on prodding were considered dead.

Mite Foliage Spray Test

Adults and nymphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

Nematode Test

Infective migratory larvae of the root-knot nematode, (*Meloidogyne incognita var. acrita*) were reared in the greenhouse on roots of Rutgers variety tomato plant. Infected tomato plants were removed from the culture and the roots were chopped very finely. A small amount of inoculum from the roots was added to pint Mason jars containing approximately 180 cc of soil. The jars containing the inoculum and soil were capped and incubated for one week at room temperature. During this period eggs of the nematode hatched and the larvae forms migrated into the soil.

The test compounds were formulated by diluting the stock suspension with water to give a suspension containing 500 parts of test compound per million parts of final formulation. 10 milliliters of the test formulation was added to each of two jars for each dosage treated. As a control 10 milliliters of a water-acetone-emulsifier solution containing no test compound was also added to jars containing nematode larvae. The jars were capped and the contents thoroughly mixed on a kale mill for five minutes. The jars remained capped at room temperature for a period of 48 hours and the contents were then transferred to 3 inch pots. Subsequently, the pots were seeded to cucumber as an indicator crop and placed in the green house where they were cared for in the normal fashion for growing potted cucumber for approximately three weeks. These cucumber plants were then removed from the pots, the soil washed from the roots and the amount of galling visually rated.

The results of these tests are set forth in Table I below. In these tests the pesticidal activity of the compounds against aphid, mite, Southern Armyworm, Bean Beetle and house fly was rated as follows:

A = excellent control
B = partial control
C = no control

The nematocidal toxicity has the following ratings;
1 = severe galling; equal to untreated control;
2 = moderate galling
3 = light galling
4 = very light galling
5 = no galling Dashes indicate no test conducted.

Certain of these compositions were also evaluated to determine their peroral toxicity to mammals. The animal selected for this experiment was the rat. The test results obtained are expressed in terms of the number of milligrams of compositions per kilogram of weight of the animal required to achieve a mortality rate of 50 percent ($LD_{50}$).

The results of all of these tests are set forth in Table I below:

TABLE I

BIOLOGICAL ACTIVITY AND PHYSICAL PROPERTIES

| COMPOUND | MP° C. | Bean Aphid | 2-Spotted Mite | Southern Armyworm | Mexican Bean Beetle | House-Fly | Root-Knot Nematode | A.O. Rat Mg/Kg |
|---|---|---|---|---|---|---|---|---|
| N,N'—Bis-[1-Methylthio acetaldehyde O—(N—methyl carbamoyl)oxime] disulfide | 87–89 | A | C | A | A | A | 1 | 190 |
| N,N'—Bis-[1-Methylsulfinyl acetaldehyde O—(N—methyl carbamoyl)oxime] disulfide | 131–133 | C | C | B | A | A | 1 | — |
| N,N'—Bis-[1-Isopropylthio acetaldehyde O—(N—methyl carbamoyl)oxime] disulfide | oil | A | A | A | A | A | 4 | — |
| N,N'—Bis-[1-(2-Cyanoethyl thioacetaldehyde O—(N—methyl carbamoyl)oxime] disulfide | oil | A | A | A | A | A | 4 | 80 |
| N,N'—Bis-[2-Methylthio-2-methylpropionaldehyde O—(N—methylcarbamoyl)oxime] disulfide | 78.5–80.5 | A | A | A | A | A | 5 | — |
| N,N'—Bis-[2-Methylsulfonyl-2-methylpropionaldehyde O—(N—methylcarbamoyl)oxime] disulfide | 130–132 | C | B | C | C | A | 4 | — |
| N,N—Bis-[2-Cyano-2-methyl-propionaldehyde O—(N—methyl-carbamoyl)oxime] disulfide | 131–132 | A | A | A | A | A | 4 | — |

TABLE I-continued
BIOLOGICAL ACTIVITY AND PHYSICAL PROPERTIES

| COMPOUND | MP° C. | Bean Aphid | 2-Spotted Mite | Southern Armyworm | Mexican Bean Beetle | House-Fly | Root-Knot Nematode | A.O. Rat Mg/Kg |
|---|---|---|---|---|---|---|---|---|
| N,N'—Bis-[2-(O—(N—Methyl-carbamoyl)oximino)-1,3-dithio-lane] disulfide | 137–140 | A | C | A | A | A | 5 | — |
| N,N'—Bis-[4-(O—(N—Methylcarba-moyl)oximino)-5-methyl-1,3-oxathiolane] disulfide | 97–105 | A | A | A | A | A | 1 | — |
| N,N'—Bis-[2-(O—(N—Methylcarba-moyl)oximino)-1,4-dithiane] disulfide | 142–144 | A | A | A | A | A | 1 | 160 |
| N,N'—Bis-[2-Methylimino-4,4-dimethyl-5-(O—(N—methyl-carbamoyl)oximino-1,3-dithiolane] disulfide | 113–115 | A | B | A | A | A | 4 | — |
| N,N'—Bis-[3-Isopropyl-5,5-dimethyl-2-(O—(N—methyl carbamoyl)oximino)-1,3-thiazolidin-4-one] disulfide | 169.5–170.5 | A | C | B | A | C | — | — |
| N,N'—Bis-[4-Methyl-2-(O—(N—methylcarbamoyl)oximino) tetrahydro-1,4-thiazin-3-one] disulfide | 194.5–198 | A | A | A | A | A | — | — |

The results set forth in TABLE I clearly show the broad spectrum pesticidal activity of the compounds of this invention, as well as their reduced mammalian toxicity. It will be understood that the insect, mite and nematode species employed in the above tests are merely representative of a wide variety of pests that can be controlled through the use of the compounds of this invention.

The compounds contemplated in this invention may be applied as insecticides, miticides and nematocides according to methods known to those skilled in the art. Pesticidal compositions containing the compounds as the active toxicant will usually comprise a carrier and-/or diluent, either liquid or solid.

Suitable liquid diluents or carriers include water, petroleum distillates, or other liquid carriers with or without surface active agents. Liquid concentrates may be prepared by dissolving one or these compounds with a nonphytotoxic solvent such as acetone, xylene or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pound of active toxicant per acre.

The pesticides contemplated herein prevent attack by insects, nematodes and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least such decomposition, oxidation, and hydrolysis as would materially decrease the desirable pesticidal characeristic of the toxicants or impart undersirable characteristics, for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds.

What is claimed is:

1. A compound of the formula:

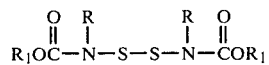

wherein:
R is alkyl having from 1 to 4 carbon atoms;
R₁ is:

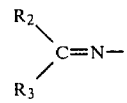

wherein:

R$_2$ is hydrogen, chloro, cyano, alkyl, alkylthio, cyanoalkylthio;

R$_3$ is alkyl, alkylthio, alkoxy, alkanyol, benzoyl alkoxycarbonyl, alkylsulfinyl, alkylsulfonyl, alkenyl, alkynyl or phenyl all of which may be substituted with one or more cyano, nitro, fluoro, bromo, chloro, alkylthio, alkylsulfinyl, alkylsulfonyl, alkoxy, phenoxy, carbamoyl, alkylcarbamoyl, dialkylcarbamoyl or

wherein:

R$_4$ is hydrogen or alkyl;

R$_5$ is hydrogen, alkyl, alkoxy or alkylthio;

with the proviso that R$_2$, R$_3$, R$_4$ and R$_5$ substituents individually may not include more than eight aliphatic carbon atoms.

2. A compound according to claim 1 wherein R is methyl.

3. A compound according to claim 1 wherein R$_2$ is hydrogen, alkyl, alkylthio or cyanoalkylthio.

4. A compound according to claim 1 wherein R$_2$ is hydrogen or alkyl.

5. A compound according to claim 1 wherein R$_3$ is alkyl, alkylthio, alkylsulfinyl, alkylsulfonyl, alkoxycarbonyl, carbamoyl, alkylcarbamoyl, dialkylcarbamoyl, alkylthioalkyl, alkylsulfinylalkyl, alkylsulfonylalkyl, cyanoalkyl, nitroalkyl, cyanoalkylthio, alkanoyl or benzoyl.

6. A compound according to claim 1 wherein R$_3$ is alkylthio, alkylsulfinyl, alkylsulfonyl, alkylsulfonyl, cyanoalkylthio, alkylthioalkyl, alkylsulfinylalkyl, alkylsulfonyl alkyl or cyanoalkyl.

7. N,N'-Bis-[1-Methylthioacetaldehyde O-(N-methylcarbamoyl)oxime]disulfide.

8. N,N'-Bis-[1-(2-cyanoethylthio)acetaldehyde O-(N-methylcarbamoyl)oximino]disulfide.

9. An insecticidal, miticidal and nematocidal composition comprising an acceptable carrier and as the active toxicant and insecticidally, miticidally or nematocidally effective amount of a compound of the formula:

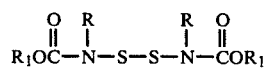

wherein:

R is alkyl having from 1 to 4 carbon atoms;

R$_1$ is

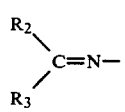

wherein:

R$_2$ is hydrogen, chloro, cyano, alkyl, alkylthio, cyanoalkylthio;

R$_3$ is alkyl, alkylthio, alkoxy, alkanoyl, benzoyl, alkoxycarbonyl, alkylsulfinyl, alkylsulfonyl, alkenyl, alkynyl or phenyl all of which may be substituted with one or more cyano, nitro, fluoro, bromo, chloro, alkylthio, alkylsulfinyl, alkylsulfonyl, alkoxy, phenoxy, carbamoyl, alkylcarbamoyl, dialkylcarbamoyl or

wherein:

R$_4$ is hydrogen or alkyl;

R$_5$ is hydrogen, alkyl, alkoxy or alkylthio;

with the proviso that R$_2$, R$_3$, R$_4$ and R$_5$ individually may not include more than eight aliphatic carbon atoms.

10. A composition according to claim 9 wherein R is methyl.

11. A composition according to claim 9 wherein R$_2$ is hydrogen, alkyl, alkylthio or cyanoalkylthio.

12. A composition according to claim 9 wherein R$_2$ is hydrogen or alkyl.

13. A composition according to claim 9 wherein R$_3$ is alkyl, alkylthio, alkylsulfinyl, alkylsulfonyl, alkoxycarbonyl, carbamoyl, alkylcarbamoyl, dialkylcarbamoyl, alkylthioalkyl, alkylsulfinylalkyl, alkylsulfonylalkyl cyanoalkyl, nitroalkyl, cyanoalkylthio, alkanoyl or benzoyl.

14. A composition according to claim 9 wherein R$_3$ is alkylthio, alkylsulfinyl, alkylsulfonyl, cyanoalkylthio, alkylthioalkyl, alkylsulfinylalkyl, alkylsulfonylalkyl or cyanoalkyl.

15. A composition according to claim 9 wherein the active toxicant is N,N'-Bis-[1-methylthioacetaldehyde O-(N-methylcarbamoyl)oxime]disulfide.

16. A composition according to claim 9 wherein the active toxicant is N,N'-bis-[1-(2-cyanoethylthio)acetaldehyde O-(N-methylcarbamoyl)oximino]disulfide.

17. A method of controlling insects, mites and nematodes which comprises subjecting them to an insecticidally, miticidally or nematocidally effective amount of a compound of the formula:

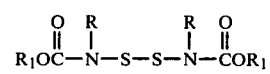

wherein:

R is alkyl having from 1 to 4 carbon atoms;

R$_1$ is:

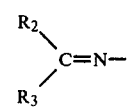

wherein:

R$_2$ is hydrogen, chloro, cyano, alkyl, alkylthio, cyanoalkylthio;

R$_3$ is alkyl, alkylthio, alkoxy, alkanoyl, benzoyl, alkoxycarbonyl, alkylsulfinyl, alkylsulfonyl, alkenyl, alkynyl or phenyl all of which may be substituted with one or more cyano, nitro, fluoro, bromo, chloro, alkylthio, alkylsulfinyl, alkylsulfonyl, alkoxy, phenoxy, carbamoyl, alkylcarbamoyl, dialkylcarbamoyl or

wherein:
R₄ is hydrogen or alkyl;
R₅ is hydrogen, alkyl, alkoxy or alkylthio;
With the proviso that $R_2$, $R_3$, $R_4$, $R_5$ substituents individually may not include more than eight aliphatic carbon atoms.

18. A method according to claim 17 wherein R is methyl.

19. A method according to claim 17 wherein $R_2$ is hydrogen, alkyl, alkylthio or cyanoalkylthio.

20. A method according to claim 17 wherein $R_2$ is hydrogen or alkyl.

21. A method according to claim 17 wherein $R_3$ is alkyl, alkylthio, alkylsulfinyl, alkylsulfonyl, alkoxycarbonyl, carbamoyl, alkylcarbamoyl, dialkylcarbamoyl, alkylthioalkyl, alkylsulfinylalkyl, alkylsulfonylalkyl, cyanoalkyl, nitroalkyl, cyanoalkylthio alkanoyl or benzoyl.

22. A method according to claim 17 wherein $R_3$ is alkylthio, alkylsulfinyl, alkylsulfonyl, cyanoalkylthio, alkylthioalkyl, alkylsulfinylalkyl, alkylsulfonylalkyl or cyanoalkyl.

23. A method according to claim 17 wherein the compound is N,N'-bis-[1-Methylthioacetaldehyde O-(N-methylcarbamoyl)oxime]disulfide.

24. A method according to claim 17 wherein the compound is N,N'-bis-[1-(2-Cyanoethylthio)acetaldehyde O-(N-methylcarbamoyl)oximino]disulfide.

25. A compound of the formula

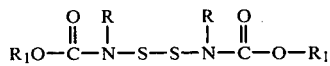

R is alkyl having 1 to 4 carbon atoms
$R_1$ is

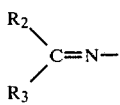

wherein
$R_2$ is $C_1$ to $C_8$ alkyl
$R_3$ is $C_1$ to $C_8$ alkylthio.

26. N,N'-bis-[1-Isopropylthioacetaldehyde O-(N-methylcarbamoyl)oxime]disulfide.

27. An insecticidal composition comprising an acceptable carrier, and as the active toxidant, an insecticidally effective amount of a compound of the formula:

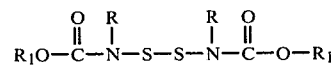

wherein
R is alkyl having 1-4 carbon atoms
$R_1$ is

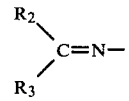

$R_2$ is $C_1$–$C_8$ alkyl
$R_3$ is $C_1$–$C_8$ alkylthio.

28. A method of controlling insects which comprises subjecting them to an insecticidally effective amount of a compound of the formula:

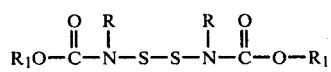

wherein
R is alkyl having 1-4 carbon atoms
$R_1$ is

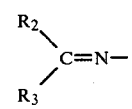

$R_2$ is $C_1$–$C_8$ alkyl
$R_3$ is $C_1$–$C_8$ alkylthio.

29. A method of preparing a compound of the formula:

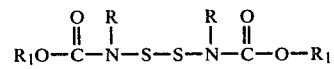

which comprises reacting two equivalents of a compound of the formula:

$R_1OH$ with one equivalent of a compound of the formula:

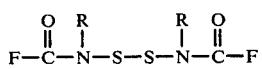

in the presence of at least two equivalents of an acid acceptor wherein
R is alkyl having 1-4 carbon atoms
$R_1$ is

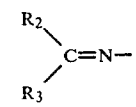

$R_2$ is $C_1$–$C_8$ alkyl
$R_3$ is $C_1$–$C_8$ alkylthio.

* * * * *